(12) United States Patent
Sharma (10) Patent No.: US 9,994,317 B2
(45) Date of Patent: Jun. 12, 2018

(54) AVIATION MASK

(71) Applicant: AIRBUS GROUP INDIA PRIVATE LIMITED, Bangalore (IN)

(72) Inventor: Anurag Sharma, Bangalore (IN)

(73) Assignee: AIRBUS GROUP INDIA PRIVATE LIMITED, Bangalore, Karnataka (IN)

( * ) Notice: Subject to any disclaimer, the term of this patent is extended or adjusted under 35 U.S.C. 154(b) by 224 days.

(21) Appl. No.: 15/164,904

(22) Filed: May 26, 2016

(65) Prior Publication Data

US 2016/0355262 A1 Dec. 8, 2016

(30) Foreign Application Priority Data

Jun. 2, 2015 (IN) ............................ 2778/CHE/2015
Sep. 4, 2015 (IN) ............................ 4701/CHE/2015
Oct. 1, 2015 (IN) ............................ 5270/CHE/2015

(51) Int. Cl.
| | |
|---|---|
| *G06T 19/00* | (2011.01) |
| *A62B 18/02* | (2006.01) |
| *A62B 18/00* | (2006.01) |
| *A62B 9/00* | (2006.01) |
| *B64D 10/00* | (2006.01) |

(Continued)

(52) U.S. Cl.
CPC ................ *B64D 11/00* (2013.01); *A62B 7/14* (2013.01); *A62B 9/006* (2013.01); *A62B 18/02* (2013.01); *A62B 18/025* (2013.01); *A62B 18/08* (2013.01); *G02B 27/0093* (2013.01); *G02B 27/017* (2013.01); *G06F 3/013* (2013.01); *G06F 3/16* (2013.01); *G06T 19/006* (2013.01); *A61B 3/113* (2013.01); *B64D 2231/025* (2013.01)

(58) Field of Classification Search
CPC ..... G06T 19/006; A62B 18/025; A62B 9/006; A62B 18/02; A62B 18/08; A62B 7/14; B64D 2231/025; B64D 10/00; B64D 11/00; G02B 27/017; G02B 27/0093; G06F 3/013; G06F 3/16
USPC ....................... 345/633, 8; 359/630; 381/367
See application file for complete search history.

(56) References Cited

U.S. PATENT DOCUMENTS

| | | | |
|---|---|---|---|
| 4,832,287 A * | 5/1989 | Werjefelt .................. | B60R 1/00 244/118.5 |
| 7,525,448 B1 * | 4/2009 | Wilson ................... | G02B 27/01 340/461 |

(Continued)

*Primary Examiner* — Jin-Cheng Wang
(74) *Attorney, Agent, or Firm* — Prakash Nama; Global IP Services, PLLC (57) ABSTRACT

An aviation mask is disclosed which includes a first set of sensors that monitors cockpit ambient air and health of an aircraft crew member for detecting parameters that cause respiratory disorder to the aircraft crew member an oxygen regulator that switches between a dilution mode, an emergency mode, and a recirculation mode to supply respiratory gas to the aircraft crew member, an augmented reality visor, a second set of sensors that detects a portion of a cockpit area that is viewed by the aircraft crew member, and a display computational unit that projects a prestored image associated with the portion onto the augmented reality visor which is superimposed over the portion of the cockpit area. The first set of sensors also monitors aircraft cockpit area for detecting vision obscured emergencies. The superimposed prestored image is used to identify objects in the portion during the vision obscured emergency.

29 Claims, 3 Drawing Sheets

(51) Int. Cl.
*B64D 11/00* (2006.01)
*G02B 27/01* (2006.01)
*A61M 16/06* (2006.01)
*G06F 3/16* (2006.01)
*G06F 3/01* (2006.01)
*G02B 27/00* (2006.01)
*A62B 7/14* (2006.01)
*A62B 18/08* (2006.01)
*A61B 3/113* (2006.01)

(56) References Cited

U.S. PATENT DOCUMENTS

| | | | |
|---|---|---|---|
| 2003/0002164 A1* | 1/2003 | McDonald | A62B 9/006 359/630 |
| 2011/0001796 A1* | 1/2011 | Werjefelt | B64D 43/00 348/47 |
| 2014/0266985 A1* | 9/2014 | Harrison | G09G 3/20 345/8 |
| 2015/0151838 A1* | 6/2015 | Kerns | B64D 25/00 345/633 |
| 2016/0019808 A1* | 1/2016 | Chavez | G09B 9/302 434/38 |
| 2016/0048725 A1* | 2/2016 | Holz | G01P 13/00 345/156 |
| 2016/0093230 A1* | 3/2016 | Boggs | G09B 9/302 434/38 |

* cited by examiner

AVIATION MASK

RELATED APPLICATIONS

Benefit is claimed under 35 U.S.C. 119(a)-(d) to Foreign application Serial No. 5270/CHE/2015 filed in India entitled "AVIATION MASK", on Oct. 1, 2015, by AIRBUS GROUP INDIA PRIVATE LIMITED, which is herein incorporated in its entirety by reference for all purposes.

CROSS-REFERENCE TO RELATED APPLICATIONS

This application claims priority to Indian Application Number 2778/CHE/2015 filed on Jun. 2, 2015 and entitled "respiratory masks for use in aircrafts" and an Indian Application Number 4701/CHE/2015 filed on Sep. 4, 2015 and entitled "aviation mask".

TECHNICAL FIELD

Embodiments of the present subject matter generally relate to masks, and more particularly, to aviation mask.

BACKGROUND

Crew members in a cockpit area of an aircraft may suffer from several dangerous and catastrophic emergencies. For example, the crew members may suffer from respiratory related emergencies, such as hyperventilation and hypoxia. These emergencies may occur due to smoke in the cockpit, reduction in pressure level due to height of the aircraft, workload/stress, and/or the like. For example, smoke in the cockpit may occur due to short circuit, equipment failure, insulation breakdown, and the like.

Typically, during respiratory related emergencies, the crew member may be provided with a respiratory mask and further, the crew member may have to manually operate an oxygen regulator of the respiratory mask to obtain the needed respiratory gases for a smooth respiration. Manual operation of the oxygen regulator may not be possible in respiratory related emergencies, such as smoky environments, due to heavy workload and/or difficulty in locating switches for suppressing the smoke. Also, manual operation of the oxygen regulator in respiratory related emergencies may need crew member's attention, which may result in distracting the crew member from other needed vital operations.

Further, vision obscured emergencies may also occur in the cockpit area which may cause vision impairment to aircraft crew members in the cockpit. The vision obscured emergencies may be caused by several factors, such as fumes, smoke, mist, leakage of toxic/corrosive liquid of wipers, smoke due to avionics fire, smoke due to electrical short circuits, fumes or smokes due to engine failure, and the like. During such vision obscured emergencies, an aircraft crew member, for example a pilot, may wear a mask to facilitate respiration and to protect eyes from smokes, fumes, toxic liquids, and/or irritants. However, the aircraft crew member when wearing the mask under these conditions may not be able to clearly see control panel located in the cockpit area. Further in such conditions when wearing the mask, the aircraft crew member may not be able to get a good view of objects located outside the aircraft, especially through a windshield of the aircraft. Furthermore, due to the poor visibility inside the cockpit, the aircraft crew member may inadvertently actuate an undesired switch/control, while operating the aircraft for controlling the aircraft during such vision obscured emergencies.

SUMMARY

An aviation mask is disclosed. According to one aspect of the present subject matter the aviation mask may include at least one first set of sensors, an oxygen regulator, an augmented reality visor, at least one second set of sensors, and a display computational unit. The at least one first set of sensors may monitor cockpit ambient air and health of an aircraft crew member wearing the aviation mask for detecting parameters that cause respiratory disorder to the aircraft crew member. The at least one first set of sensors may also monitor aircraft cockpit area for detecting vision obscured emergencies. Further, the oxygen regulator may switch between operating modes to supply respiratory gas to the aircraft crew member upon detection of the parameters by the at least one first set of sensors. The operating modes comprise a dilution mode, art emergency mode, and a recirculation mode. Furthermore, the at least one second set of sensors may detect a portion of a cockpit area of an aircraft that is viewed by the aircraft crew member upon detection of the vision obscured emergency by the at least one first set of sensors. Also, the display computational unit communicatively connected to the augmented reality visor and the at least one second set of sensors. The display computational unit may project a prestored image associated with the portion of the cockpit area in front of the augmented reality visor. The display computational unit may also superimpose the prestored image over the portion of the cockpit area viewed by the aircraft crew member. The superimposed prestored image may be viewed by the aircraft crew member through the augmented reality visor to identify one or more objects in the portion of the cockpit area during the vision obscured emergency.

The aviation mask and method disclosed herein may be implemented in any means for achieving various aspects. Other features will be apparent from the accompanying drawings and from the detailed description that follow.

BRIEF DESCRIPTION OF THE DRAWINGS

Various embodiments are described, herein with reference to the drawings, wherein.

The drawings described herein are for illustration purposes only and are not intended to limit the scope of the present disclosure in any way.

DETAILED DESCRIPTION

In the following detailed description of the embodiments of the present subject matter, references are made to the accompanying drawings that form a part hereof, and in which are shown by way of illustration specific embodiments in which the present subject matter may be practiced. These embodiments are described in sufficient detail to enable those skilled in the art to practice the present subject matter, and it is to be understood that other embodiments may be utilized and that changes may be made without departing from the scope of the present subject matter. The following detailed description is, therefore, not to be taken in a limiting sense, and the scope of the present subject matter is defined by the appended claims.

Generally, an aircraft crew member of an aircraft is provided with a respiratory mask for obtaining needed respiratory gas during emergencies. Such emergencies may include smoke in a cockpit of the aircraft, pressurization loss, air contamination, and the like. However, such respiratory masks may be generally bulky and removal of the respiratory mask from a stowage located beside a seat of the aircraft crew member for wearing it may be cumbersome and may need significant time. During this process, the aircraft crew member may ends up inhaling the smoke.

Also, head-up displays (HUDs) or head-up screens are used for displaying information associated with electronic flight instruments during normal operating conditions. However, such HUDs may not be useful during the vision obscured emergencies. For example, the vision obscured emergencies (e.g., presence of smoke/fumes/fog in the cockpit area) can cause visual, disturbances in the cockpit area and may restrict the aircraft crew member to view and identify control switches inside the cockpit area.

Embodiments described herein provide an aviation mask for use by the aircraft crew member in an aircraft. The aircraft crew member may include a pilot, flight attendant, flight medic, and the like.

In an embodiment, the aviation mask may include first set of sensors for monitoring either cockpit ambient air and/or aircraft crew member's health for detecting parameters that cause respiratory disorder to the aircraft crew member. The parameters may be presence of smoke in a cockpit of the aircraft, pressure level inside the cockpit, and contaminants present in cockpit ambient air, breathing rate of an aircraft crew member in the aircraft, carbon dioxide level present in exhaled gas of the aircraft crew member, partial pressure of oxygen present in aircraft crew member's blood, and tissue oxygen saturation of the aircraft crew member. The first set of sensors may also monitor aircraft cockpit area for detecting vision obscured emergencies. The vision obscured emergencies may, for example, refer to emergency conditions inside the aircraft because of which the aircraft crew member may not be able to see the objects inside the aircraft.

Furthermore, the aviation mask may include an oxygen regulator for switching between operating modes to supply the respiratory gas to the aircraft crew member upon detection of the parameters by the first set of sensors. Example operating modes may include a dilution mode, an emergency mode and a recirculation mode. The respiratory gas may include oxygen during the emergency mode, a combination of the exhaled gas including carbon dioxide ($CO_2$) and gases already present in the mouthpiece and oxygen regulator cavity during the recirculation mode, and a combination of air inside the cockpit or air mixed with oxygen during, the dilution mode.

The aviation mask further includes an augmented reality visor, second set of sensors, and a display computational unit. The second set of sensors detects a portion of the cockpit area that is viewed by the aircraft crew member. The portion of the cockpit area is detected upon detection of the vision obscured emergency by the first set of sensors. Further, the display computational unit is communicatively connected to the augmented reality visor and the second set of sensors. The computational unit projects a prestored image associated with the portion of the cockpit area in front of the augmented reality visor. Also, the display computational unit may superimpose the prestored image over the portion of the cockpit area viewed by the aircraft crew member. The superimposed prestored image is viewed by the aircraft crew member through the augmented reality visor to identify one or more objects in the portion of the cockpit area during the vision obscured emergency.

Thus, the aviation mask functions continuously as a respiratory aid during long haul crew member operations to prevent sadden incapacitation due to the emergencies and preserves bottled oxygen supply in the aircraft. Also, the aviation mask is lightweight. Therefore, the mask can be worn by the aircraft crew member comfortably throughout the flight. The aviation mask also helps the aircraft crew member to identify objects in the portion of the cockpit area during the vision obscured emergency.

The aviation mask, in accordance with an example of the present subject matter, an aviation mask is explained in detail with reference to FIGS. 1 to 3, where the reference numerals indicate example components of the aviation mask.

Figure 1:
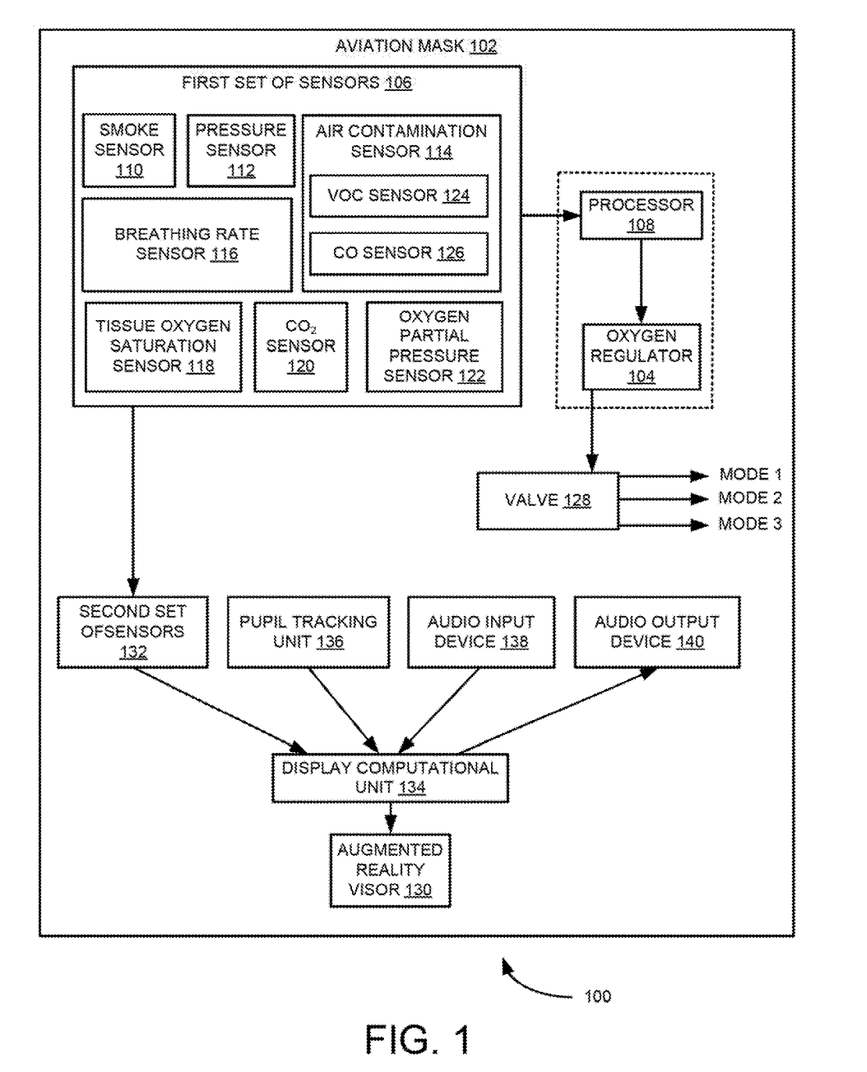
FIG. 1 is a block diagram showing an example aviation mask including components.

FIG. 1 is a block diagram 100 of an aviation mask 102, according to one embodiment. The aviation mask 102 may be worn by an aircraft crew member comfortably throughout the flight of an aircraft Example aircraft crew member may include a pilot, flight attendant, flight medic, and the like. In addition, the aviation mask 102 may be operable throughout the flight of the aircraft for protecting the aircraft crew member from several dangerous and catastrophic emergencies. For example, the emergencies may be respiratory related emergencies, such as hyperventilation, hypoxia and the like. In another example, the emergencies may be vision obscured emergencies.

In accordance with the present subject matter, the aviation mask 102 may further include an oxygen regulator 104 and first set of sensors 106. In one implementation, the oxygen regulator 104 may be electronically coupled to the first set of sensors 106 through a processor 108. In one implementation, the oxygen regulator 104 and the processor 108 may be separate components coupled to each other. In another implementation, the oxygen regulator 104 may include the processor 108. Further, the first set of sensors 106 may include smoke sensor 110, pressure sensor 112, air contamination sensor 114, breathing rate sensor 116, tissue oxygen saturation sensor 118, carbon dioxide ($CO_2$) sensor 120, and oxygen partial pressure sensor 122. In one example, the air contamination sensor 114 may include Volatile Organic Compound (VOC) sensor 124 and Carbon monoxide (CO) sensor 126. The processor 108 obtains output of the first set of sensors 106 as input which is then processed by the processor 108. The processed output is then sent to the oxygen regulator 104. The oxygen regulator 104, upon receiving the processed output, actuates one or more valves 128 for switching either to mode 1 or mode 2 or mode 3 based on the received processed output. In one embodiment, the one or more valves 128 may reside inside the oxygen regulator 104. For the purpose of simplicity of explanation, the mode 1 may be understood as an emergency mode, the mode 2 may be understood as a recirculation mode, and the mode 3 may be understood as a dilution mode. Further, actuation of the one or more valves 128 to switch either to mode 1 or mode 2 or mode 3 may help to supply a respiratory gas to the aircraft crew member. The respiratory gas may include oxygen which may be supplied during the emergency mode. The respiratory gas may also include the exhaled gas which may be supplied during the recirculation mode. The respiratory gas may further include a combination of air inside the cockpit or the cockpit ambient air progressively mixed with more oxygen as altitude increases may be supplied during the dilution mode.

Further, the oxygen regulator 104 may actuate the one or more valves 128 based on the output of the first set of sensors 106. In one example, the oxygen regulator 104 may actuate the one or more valves 128 when the output indicates emergency conditions. The emergency conditions may be understood as conditions when there is presence of smoke in the cockpit, the pressure level present inside the cockpit is lower than a predetermined pressure level, the partial pressure of the oxygen present in the aircraft crew member's blood is lower than a predetermined partial pressure of the oxygen, the carbon dioxide level present in the exhaled gas is higher than a predetermined carbon dioxide level, and/or the breathing rate of the aircraft crew member is deviated from a predetermined breathing rate.

The predetermined pressure level may be understood as a level of the pressure inside the cockpit at which the aircraft crew member can breathe comfortably without any hurdle. For example, the predetermined pressure level may be considered as a level of the pressure at a height of 6000 feet from the sea level. Similarly, the predetermined partial pressure of the oxygen may be understood as a level of the partial pressure of the oxygen at which mental acuity of the aircraft crew member may start to be affected. For example, the predetermined partial pressure of the oxygen may be in between 94% to 95%. In a like manner, for the purpose of simplicity of the explanation, the predetermined carbon dioxide level may be understood as a level of the carbon dioxide present in the exhaled gas from the body of the aircraft crew member such that the respiratory system of the aircraft crew member is healthy. Similarly, the predetermined breathing rate may be understood as breathing rate at which the aircraft crew member breathes comfortably. The breathing rate may be understood as, for example, number of breaths per minute. Alternatively, the breathing rate may be understood, for example, as an expiration volume in liter/sec or an expiration volume per breath. The mode of the aviation mask 102 in accordance with this implementation may be understood as emergency mode. Such above explained emergency conditions may result in lack of oxygen and the aircraft crew member may get respiratory disorder, such as hypoxia, due to hick of oxygen which may lead to unconsciousness of the aircraft crew member.

To overcome the respiratory disorder due to the lack of oxygen, the aircraft crew member may be forced to inhale oxygen so that the level of oxygen in the blood can be retained, to a level where the aircraft crew member can breathe smoothly. Therefore, the oxygen regulator 104 may provide oxygen to the aircraft crew member by actuating the one or more valves 128. Thus, inhalation of oxygen may protect the aircraft crew member from hypoxia caused by the above explained emergency conditions. Protection of the aircraft crew member using oxygen is nor limited only to hypoxia and inhalation of oxygen may also protect the aircraft crew member from the respiratory disorders other than hypoxia.

In another example, the oxygen regulator 104 may actuate the one or more valves 128 when the output indicates that a percentage of oxygen present in the blood of the aircraft crew member is at least 94%. The oxygen regulator 104 may also actuate the one or more valves 128 when the carbon dioxide level present in the exhaled gas is lower than the predetermined carbon dioxide level and/or when the breathing rate of the aircraft crew member is higher than the predetermined breathing rate and/or expiration volume is low which may occur during a high stress condition. In such above explained conditions, the aircraft crew member may be hyperventilating and may subsequently lead to unconsciousness of the aircraft crew member. The mode of the aviation mask 102 in accordance with this implementation may be understood as recirculation mode. To overcome the respiratory disorder caused by these conditions, the aircraft crew member may be momentarily forced to inhale the exhaled gas till the breathing rate can be controlled. The oxygen may be stored in an oxygen storage kept onboard for supplying when needed. Further, inhalation of the recirculated gas helps the brain to auto-regulate the breathing rate, thereby protecting the aircraft crew member from hyperventilation caused by the above explained conditions.

In yet another example, the oxygen regulator 104 may actuate the one or more valves 128 to the dilution mode when the output of the first set of sensors 106 indicates any one of the conditions, such as presence of no smoke/contaminants in the cockpit, the pressure level inside the cockpit is higher than a predetermined pressure level, the partial pressure of the oxygen present in the aircraft crew member's blood is higher than a predetermined partial pressure of the oxygen and/or the breathing rate of the aircraft crew member is equal to a predetermined breathing rate. The predetermined breathing rate, the predetermined carbon dioxide level, and the predetermined partial pressure of the oxygen may be understood as explained above. The dilution mode may be understood as a mode where the respiratory system of the aircraft crew member functions normally, i.e., in which there is no symptoms of either hyperventilation or hypoxia or any other respiratory disorder in the aircraft crew member.

In one example, the aviation mask 102 may be used in the vision obscured emergencies. The aviation mask 102 may be used by a pilot or other aircraft crew members, such as cabin crew, for identifying the objects in the aircraft during the vision obscured emergencies. The vision obscured emergency may be detected using the first set of sensors 106. In one example, the first set of sensors 110 may include a smoke sensor 110 to sense smoke in the aircraft for detecting the vision obscured emergency. Other types of sensors may also be used for sensing conditions inside the aircraft that can lead to the vision obscured emergency, for example a fog sensor may be used to sense fog inside the aircraft. In one example, the aviation mask 102 may include an augmented reality visor 130, second set of sensors 132, and a display computational unit 134. The portion may refer to panels, along with other components, located in the cockpit area of the aircraft. Example second set of sensors 132 may include infra red cameras, magnetic markers, electromagnetic sensors, and the like. Further, the display computational unit 134 is communicatively connected to the augmented reality visor 130 and the second set of sensors 132. The second set of sensors 132 may be connected to the first set of sensors 106. The second set of sensors 132 may detect a portion of a cockpit area when the in set of sensors 106 detect the vision obscured emergency in the cockpit area. Further, the display computational unit 134 projects a prestored image associated with the portion of the cockpit area in front of the augmented reality visor 130. The prestored image associated with the portion of the cockpit area is projected in front of the augmented reality visor 130 based on a distance between the aircraft crew member and the portion of the cockpit area. Furthermore, the display computational unit 134 superimposes the prestored image over the portion of the cockpit area viewed by the aircraft crew member. The superimposed prestored image being viewed by the aircraft crew member through the augmented reality visor 130 to identify one or more objects in the portion of the cockpit area during the vision obscured emergency. Example objects may be controls/switches/knobs/buttons on a panel of the cockpit area.

For the purpose of explanation, the portion of the aircraft may be considered as the control/display panels in cockpit area and the object may be considered as the switch/knob/button/control. However, the portion may be any parts inside the aircraft and the object may be any component on the parts inside the aircraft.

For superimposing the prestored image on the cockpit of the aircraft, the prestored image may be aligned with edges of the panel in the cockpit area of the aircraft. For example, the prestored image may be aligned with edges of the panel using magnetic markers at diagonal ends of the cockpit. Other examples of the sensors used for alignment/orientation are electric field sensors and infrared camera. First, the edges of the panel are detected using the magnetic markers, electric field sensors author infrared camera. Then, the prestored image corresponding to the panel is selected and is aligned with the panel on the augmented reality visor 130. For example, the prestored image is collimated on the augmented reality visor 130 for aligning the prestored image with the panel.

In one embodiment, the prestored image may include an image with identifiers (e.g. name of the switches/knobs/buttons) and/or control information of the switch/knob/button. The identifiers and/or control information may enable the aircraft crew member to identify that which switch/knob/button performs which function. For example, if the switch/knob/button is assigned to turn on auto-pilot mode, then the prestored image include the name and/or control information of the switch/knob/button as "auto-pilot" indicated on the prestored image. Thus, enabling the aircraft crew member to identify this switch/knob/button among all other switches/knobs/buttons for turning on the auto-pilot mode of the aircraft.

The aircraft crew member may he navigated to the desired object in the portion of the cockpit area. For this purpose, the aviation mask 102 may include a pupil tracking unit 136. The pupil tracking unit 136 may track pupil of the aircraft crew member. The tracking information may be then sent to the display computational unit 134. Upon receiving the tracking information, the display computational unit 134 may navigate the aircraft crew member through control commands displayed on the augmented reality visor 130 using the tracking information and the control command/procedural instructions selected by the aircraft crew member using an audio input device 138. In another example, the aircraft crew member may be navigated to the desired object in the portion of the cockpit area using gesture of the aircraft crew member. The aviation mask 102 may include a thermal sensor) for detecting location where the aircraft crew member is touching on the cockpit. For this purpose, the thermal sensor may sense heat of a part (e.g., finger tip) of the body of the aircraft crew member. The sensed heat is used to determine a location where the aircraft crew member is touching on the cockpit Based on the determined location, the display computational unit 134 may navigate the aircraft crew member to the object. Example thermal sensor may be IR camera. In another embodiment, an electric field sensor may be used in place of thermal sensor. The electric field sensor may sense the electric field of the finger tip of the aircraft crew member. The sensed electric field may be used by the display computational unit 134 to navigate the aircraft crew member to the object (e.g., switch/knob/control/button).

In one example, the aircraft crew member may be navigated to the objects when the aircraft crew member is looking at a different switch/knob. The tracking information may be used to determine that the aircraft crew member is looking at the different switch/knob. For example, head position or eye position of the crew member is tracked for determining that the aircraft crew member is looking at which switch/knob. For example, the head movement may be tracked using inertial/tilt sensors. For navigating the aircraft crew member to the objects, the display computational unit 134 may interact with the audio input device 138, such as a microphone. The audio input device 134 may be provided to enable the aircraft crew member to input an audio command for selecting the control command, such as procedural instructions having steps to be followed during the vision obscured emergencies. In one example, the control command/procedural instruction may be stepwise scrolled and/or read out using voice or gesture interaction. In one embodiment, the display computational unit 134 overlays control commands on the augmented reality visor 130. In one embodiment, the aviation mask 102 may include an audio output device 140 which may communicate with the display computational unit 134 to read out the overlaid control commands. The aircraft crew member may select a control command from these control commands. The display computational unit 134 may utilize the control command selected by the aircraft crew member to navigate the aircraft crew member to the object corresponding to the control command. In one example, the display computational unit 134 may navigate the aircraft crew member to the switch/knob/button using a pointer (e.g., an arrow mark) pointing towards the switch/knob/button and/or a highlighter, for example a highlighted circle overlaid on the switch which is to be operated.

Further, in one embodiment, the display computational unit 134 may overlay information associated with aircraft's surroundings on the augmented reality visor 130. The information associated with the aircraft's surroundings may be obtained by sensors connected to an outer surface of the aircraft. Further, the display computational unit 134 may be operatively coupled to a flight management system not shown in the figures). The flight management system may send flight management information associated with the aircraft to the display computational unit 134. In some examples, the flight management information may include autopilot data, flight director information, flight path vector, boresight, Differential Global Positioning System (DGPS) or Global Positioning System (GPS) data, positioning data, aircraft speed, aircraft altitude, track to nearby airports, inertial navigation data, data associated with configuration of the aircraft, and a frequency for radio communication with a ground-based flight control. The display computational unit 134 may display the flight management information on the augmented reality visor 104, thereby enabling the aircraft crew member to control the aircraft during the vision obscured emergency.

Figure 2:
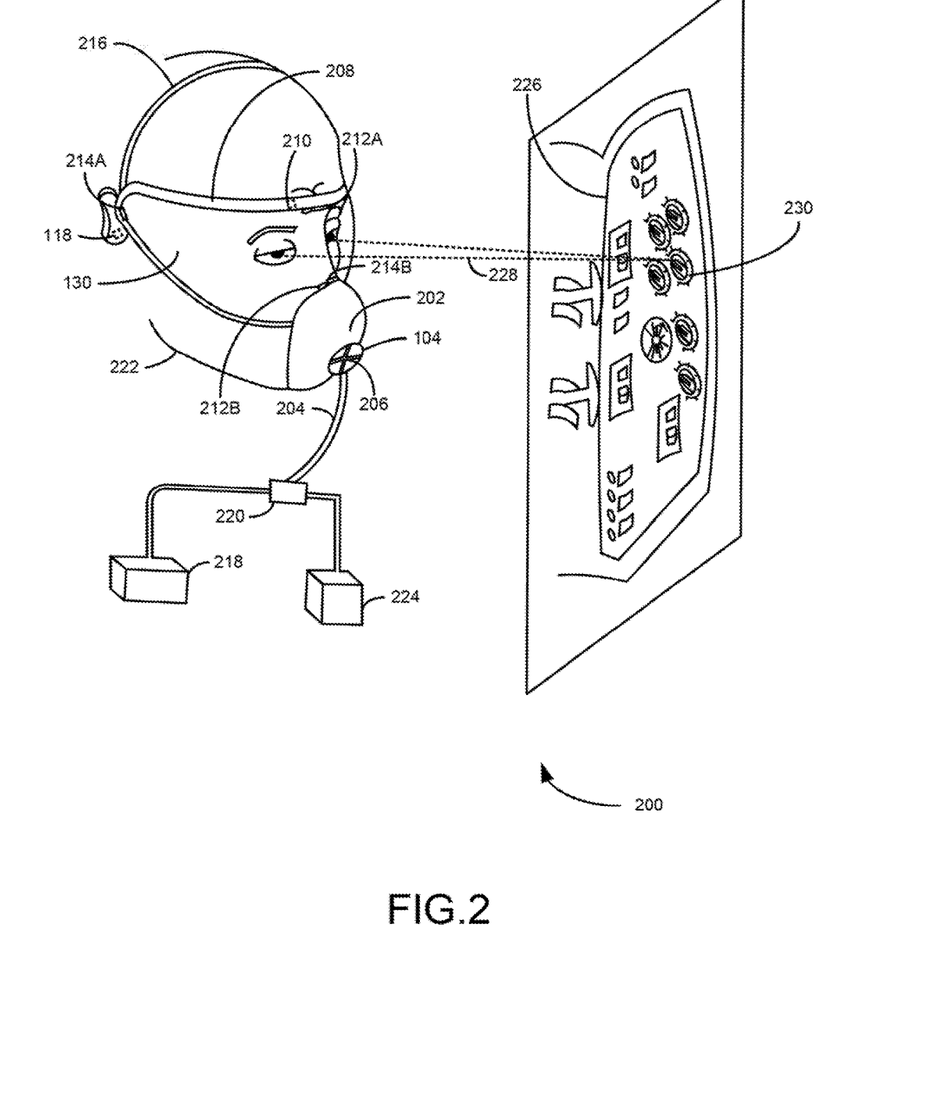
FIG. 2 is a perceptive view of an example aviation mask, such as those shown in FIG. 1.

Referring now to FIG. 2 which illustrates a perspective view of an aviation mask 102, in accordance with an embodiment. As illustrated in FIG. 2, the aviation mask 102 may include a mouth and nose piece 202 connected to a oxygen regulator 104 similar to as illustrated in FIG. 1. The mouth and nose piece 202 may have smoke sensors 110 (similar to as illustrated in FIG. 1) for sensing presence of smoke in a cockpit of the aircraft and may also have pressure sensors 112 (similar to as illustrated in FIG. 1) for sensing the pressure level present inside the cockpit. The smoke sensors 110 and the pressure sensors 112 may be mounted, for example, around the mouth and nose piece 202. For example, the smoke sensors 110 may be mounted on the oxygen regulator 104. The smoke sensors 110 are explained to be mounted on the oxygen regulator 104 for the purpose of explanation and can be mounted anywhere on the aviation mask 102 or can be mounted anywhere in the cockpit for sensing the smoke in the cockpit. Further, the aviation mask 102 may include a respiratory gas inlet 204 and a respiratory gas outlet 206. The respiratory gas inlet 204 and the respiratory gas outlet 206 may be connected to the mouth and nose piece 202 for inhaling the respiratory gas and exhaling the exhaled gas respectively. The respiratory gas inlet 204 may include breathing rate sensors 116 (similar to as illustrated in FIG. 1) disposed therein for sensing a breathing rate of an aircraft crew member in the aircraft. Similarly, the respiratory gas outlet 206 ma include carbon dioxide sensors 120 (similar to as illustrated in FIG. 1) disposed therein for sensing a carbon dioxide level in an exhaled gas by the aircraft crew member. Further, the aviation mask 102 may include an audio input device 138, for example a microphone, attached to the mouth and nose piece 202. In another example, the audio input device 138 may be inbuilt with the mouth and nose piece 202.

Further, the aviation mask 102 as illustrated in FIG. 2 may include a peripheral face seal 208. The peripheral face seal 208 may be fitted to the augmented reality visor 130. The augmented reality visor 130 is removably attached to the aviation mask 102 with the help of coupling elements 214A and 214B. Further, the peripheral face seal 208 enables to isolate or seal off the thee of the aircraft crew member from the surrounding, air for protecting the face from contaminates present in air of cockpit and heat generated by fumes or smoke. The peripheral face seal 208 may be made of, for example, pliable/compliant materials. Furthermore, the peripheral thee seal 208 may include a demist sensor 210, disposed thereon, for sensing the mist on the augmented reality visor 130. The demist sensor 210 may be communicatively coupled to the oxygen regulator 104 for providing a feedback to the oxygen regulator 104 that there is a mist on the augmented reality visor 130 and hence demisting is needed. The oxygen regulator 104, upon receiving the feedback, may perform demisting to clear mist in the augmented reality visor 130 by opening two valves 212A and 212B. One valve 212A is located, for example, on the upper portion of the face seal 208 and the other valve 212B is located on the mouth and nose piece 202. The valve 212B is connected to the oxygen regulator 104 to increase ventilation flow. The valve 212B allows oxygen/respiratory gas in and the other valve 212A allows the air with moisture out when opened. Also, the oxygen regulator 104 may be electronically coupled to the smoke sensor 110. The oxygen regulator 104 may receive output from the smoke sensor 110 and supply a respiratory gas to the aircraft crew member based on the output of the smoke sensor. The respiratory gas may be supplied to the aircraft crew member via the mouth and nose piece 202. In one example, the respiratory gas may be oxygen.

In one embodiment, the aviation mask 102 may also include a clamping mechanism 216 for facilitating the aircraft crew member to wear the aviation mask 102. The clamping mechanism 216, for example, may be straps connected to each other in such a manner that they can be utilized, for wearing the aviation mask 102. In one example, the clamping mechanism 216 may be an adjustable strap or band which can be fitted around the head of the aircraft crew member to wear the aviation mask 102.

Further, the aviation mask 102 may be connected to an oxygen supply source 218 through one or more supply valves 220. The oxygen supply source 218 may be utilized to deliver oxygen to the aircraft crew member when there is demand for oxygen, such as during emergency mode and recirculation mode. For delivering oxygen to the aircraft crew member, the oxygen regulator 104 may actuate the one or more valves 128 to enable flow of oxygen from the oxygen supply source 218 to the aircraft crew member through the respiratory gas inlet 204 and the mouth and nose piece 202. During emergency mode, the respiratory gas may include 100% oxygen supplied from the oxygen supply source 218. Whereas, during recirculation mode, the respiratory gas may include a combination of oxygen from the oxygen supply source 218 and exhaled gas by an aircraft crew member 222.

Furthermore, in accordance with an embodiment of the present subject matter, the aviation mask 102 may be connected to a purified air supply source 224 through the one or more supply valves 220. The purified air supply source 224 may be utilized to supply purified air to the aircraft crew member when air inside the cockpit is contaminated by contaminants, such as Volatile Organic Compounds (VOC) and Carbon Monoxide (CO), The purified air supply source 224 may purify the air inside the cockpit to eliminate contaminants from the air and generate a purified air. The purified, air is then supplied to the aircraft crew member by the purified air supply source 224 through the respiratory gas inlet 204 and the mouth and nose piece 202. In one implementation, the purified air is supplied during the dilution mode which preserves consumption of oxygen from the oxygen storage. In accordance with another embodiment of the present subject matter, the aviation mask 102 may include a filter unit (not shown the figures) in the mouth and nose piece 202 to filter the air inside the cockpit and provide purified/filtered an to the aircraft crew member.

In one embodiment, the augmented reality visor 130 enables the aircraft crew member 222 to see a switch 230 which the aircraft crew member 222 may want to activate. The augmented reality visor 130 may be associated with the display computational unit 134, such as those shown in FIG. 1, for collimating a presumed image 226 of the panel in the cockpit area. In one example, a pointer 228 or a highlighter, such as a circle shaped highlighted area may point towards the switch 230 in the prestored image 226 overlaid on the augmented reality visor 130 for navigating the aircraft crew member 222 to the switch 230. For example, the aircraft crew member 222 may be directed to the switch 230 using the control command selected by the aircraft crew member 222 using the microphone during the vision obscured emergency.

The aviation mask 102 may start functioning when it is removed from a stowage located beside a seat of the aircraft crew member 222. Further, aviation mask 102 may be wearable during entire flight time due to its light weight. Furthermore, the aviation mask 102 may be capable to operate in either emergency mode or recirculation mode or dilution mode which reduces consumption of oxygen from the oxygen storage and hence enables the aircraft crew member 222 to wear the aviation mask 102 during entire flight time without any interruption in the supply of the respiratory gas.

Figure 3:
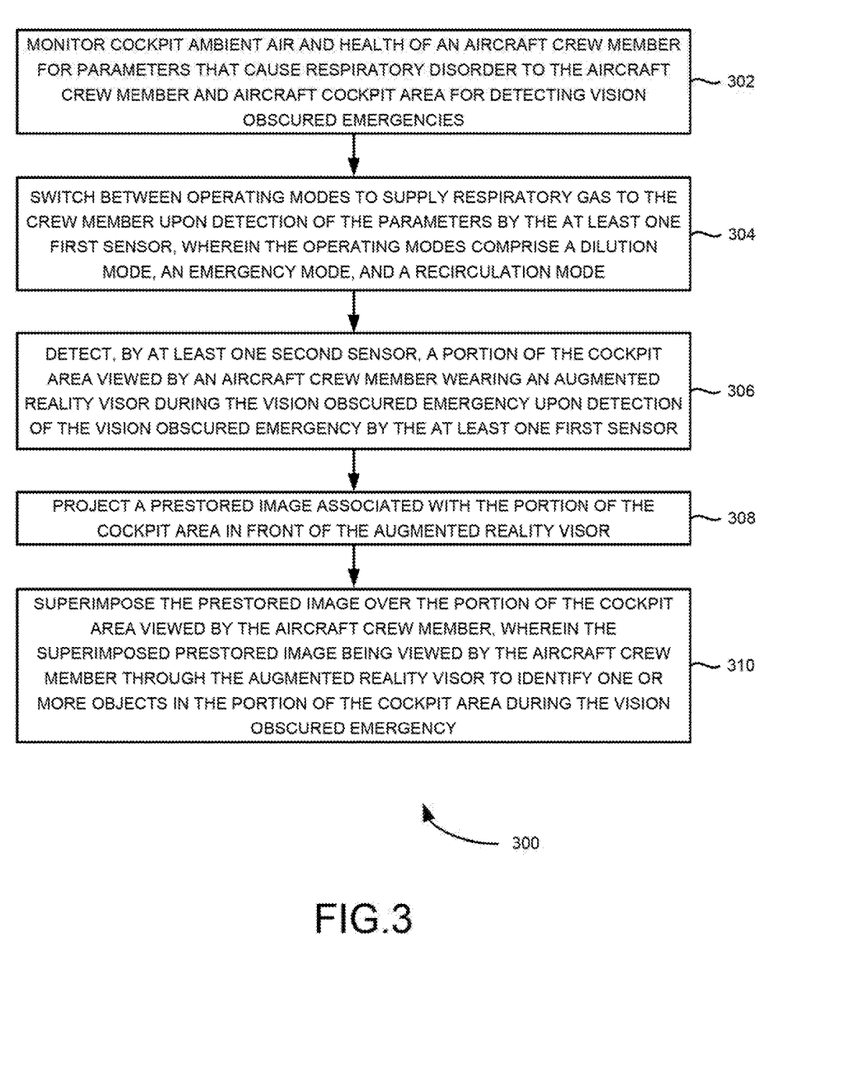
FIG. 3 is a flow diagram illustrating an example method for switching between operating modes of an aviation mask and identifying objects inside the aircraft during a vision obscured emergency, in accordance with the present subject matter.

Referring now to FIG. 3 which is a flow diagram 300 illustrating an example method for switching between operating modes of an aviation mask and identifying objects inside the aircraft during a vision obscured emergency, in accordance with the present subject matter. At step 302, cockpit ambient air and health of an aircraft crew member and aircraft cockpit area are monitored. The cockpit ambient air and health of the aircraft crew member is monitored for parameters that cause respiratory disorder to the aircraft crew member. The aircraft cockpit area is monitored for detecting vision obscured emergencies.

At step 304, operating modes may be switched to supply respiratory tins to the aircraft crew member upon detection of the parameters by the at least one first set of sensors. The operating modes comprise a dilution mode, an emergency mode, and a recirculation mode. The dilution mode, the emergency mode, and the recirculation mode may be understood as explained above.

At step 306, a portion of the cockpit area viewed by an aircraft crew member wearing an augmented reality visor during the vision obscured emergency is detected using at least one second set of sensor. The portion of the cockpit area is detected upon detection of the vision obscured emergency by the at least one first set of sensors.

At step 308, a prestored image associated with the portion of the cockpit area is projected in front of the augmented reality visor.

At step 310, the prestored image over the portion of the cockpit area viewed by the aircraft crew member is superimposed. The superimposed prestored image is viewed by the aircraft crew member through the augmented reality visor to identify one or more objects in the portion of the cockpit area during the vision obscured emergency.

It may be noted that the above-described examples of the present solution is for the purpose of illustration only. Although the solution has been described in conjunction with a specific embodiment thereof, numerous modifications may be possible without materially departing from the teachings and advantages of the subject matter described herein. Other substitutions, modifications and changes may be made without departing from the spirit of the present solution. All of the features disclosed in this specification (including any accompanying claims, abstract and drawings), and/or all of the steps of any method or process so disclosed, may be combined, in any combination, except combinations Where at least some of such features and/or steps are mutually exclusive.

The terms "include," "have," and variations thereof, as used herein, have the same meaning as the terra "comprise" or appropriate variation thereof. Furthermore, the term "based on", as used herein, means "based at least in part on."

The present description has been shown and described with reference to the foregoing examples. It is understood, however, that other forms, details, and examples can be made without departing from the spirit and scope of the present subject matter that is defined in the following claims.

What is claimed is:

1. An aviation mask comprising:
   at least one first set of sensors for monitoring at least one of:
      cockpit ambient air and health of an aircraft crew member wearing the aviation mask for detecting parameters that cause respiratory disorder to the aircraft crew member; and
      aircraft cockpit area for detecting vision obscured emergencies;
   an oxygen regulator for switching between operating modes to supply respiratory gas to the aircraft crew member upon detection of the parameters by the at least one first set of sensors, wherein the operating modes comprise a dilution mode, an emergency mode, and a recirculation mode;
   an augmented reality visor;
   at least one second set of sensors for detecting a portion of a cockpit area of an aircraft that is viewed b the aircraft crew member upon detection of the vision obscured emergency by the at least one first set of sensors; and
   a display computational unit communicatively connected to the augmented reality visor and the at least one second set of sensors, wherein the display computational unit adapted to:
      project a prestored image associated with the portion of the cockpit area onto the augmented reality visor; and
      superimpose the prestored image over the portion of the cockpit area viewed by the aircraft crew member, wherein the superimposed prestored image being viewed by the aircraft crew member through the augmented reality visor to identify one or more objects in the portion of the cockpit area during the vision obscured emergency.

2. The aviation mask of claim 1, wherein the parameters are selected from the group consisting of presence of smoke in a cockpit area of the aircraft, pressure level inside the cockpit area, contaminants present in the cockpit ambient air, breathing rate of the aircraft crew member, carbon dioxide level present in exhaled gas of the aircraft crew member, partial pressure of oxygen present in blood of the aircraft crew member, and tissue oxygen saturation of the aircraft crew member.

3. The aviation mask of claim 1, wherein the oxygen regulator is configured to:
   switch to the emergency mode when at least one emergency condition occurs, wherein the at least one emergency condition is selected from the group consisting, of presence of smoke in the cockpit area, pressure level inside the cockpit area is lower than a predetermined pressure level, partial pressure of oxygen present in blood of the aircraft crew member is lower than a predetermined partial pressure of oxygen, carbon dioxide level present in exhaled gas is higher than a predetermined carbon dioxide level, breathing rate of the aircraft crew member is deviated from a predetermined breathing rate, and tissue oxygen saturation of the aircraft crew member is lower than a predetermined tissue oxygen saturation.

4. The aviation mask of claim 1, wherein the oxygen regulator is configured to:
   switch to the recirculation mode when a percentage of oxygen in blood of the aircraft crow member is at least 94% and one of carbon dioxide level present in exhaled gas is lower than a predetermined carbon dioxide level and breathing rate of the aircraft crew member is higher than a predetermined breathing rate.

5. The aviation mask of claim 1, wherein the oxygen regulator is configured to:
   switch to the dilution mode when at least one condition occurs, wherein the at least one condition comprises no smoke present in the cockpit area, pressure level inside the cockpit area is higher than a predetermined pressure level, breathing rate of the aircraft crew member is equal to a predetermined breathing rate, carbon dioxide level present in exhaled gas is equal to a predetermined carbon dioxide level, and partial pressure of oxygen present in blood of the aircraft crew member is equal to a predetermined partial pressure of oxygen.

6. The aviation mask of claim 1, wherein the respiratory gas comprises one of oxygen during, the emergency mode, a combination of exhaled gas and oxygen during the recirculation mode, and the cockpit ambient air during the dilution mode.

7. The aviation mask of claim 1, further comprising:
a mouth and nose piece connected to the oxygen regulator;
a respiratory gas inlet and a respiratory gas outlet connected to the mouth and nose piece, wherein at least one breathing rate sensor from the at least one first set of sensors is disposed in the respiratory gas inlet for sensing breathing rate of the aircraft crew member and wherein at least one carbon dioxide sensor from the at least one first set of sensors is disposed in at least one of the respiratory gas outlet and the mouth and nose piece for sensing carbon dioxide level present in exhaled gas.

8. The aviation mask of claim 1, further comprising:
a peripheral face seal, wherein the at least one first set of sensors is disposed around the peripheral face seal for sensing partial pressure of oxygen present in blood of the aircraft crew member.

9. The aviation mask of claim 1, wherein the prestored image comprises an image of the portion of the aircraft with identifiers and/or control information of the one or more objects.

10. The aviation mask of claim 1, wherein the portion of the aircraft comprises at least one control on a control panel in the cockpit area of the aircraft.

11. The aviation mask of claim 1, wherein the display computational unit superimposes the prestored image over the portion of the cockpit area viewed b the aircraft crew member by:
detecting edges of the portion of the cockpit area using the at least one second set of sensors; and
aligning the projected prestored image of the portion of the cockpit area over the portion of the cockpit area viewed by the aircraft crew member.

12. The aviation mask of claim 1, wherein the display computational unit overlays a plurality of control commands or procedural instructions on the augmented reality visor to enable the aircraft crew member to select one or more control commands or a procedural instruction.

13. The aviation mask of claim 12, further comprising:
a pupil tracking unit to track pupil of the aircraft crew member, wherein the display computational unit enables the aircraft crew member to navigate through the control commands displayed on the augmented reality visor based on the tracking information and the one or more control commands or the procedural instruction selected by the aircraft crew member.

14. The aviation mask of claim 12, further comprising:
at least one third set of sensors to track head position or eye position of the aircraft crew member, wherein the display computational unit enables the aircraft crew member to select a cockpit control and provides directions to the aircraft crew member to navigate to the selected cockpit control based on the head position or the eye position.

15. The aviation mask of claim 12, further comprising:
an audio input device to enable the aircraft crew member to select one or more control commands or the procedural instruction.

16. The aviation mask of claim 12, further comprising:
an audio output device to read out the plurality of the control commands or the procedural instructions.

17. A method comprising:
monitoring, by at least one first set of sensors, at least one of:
cockpit ambient air and health of an aircraft crew member for parameters that cause respiratory disorder to the aircraft crew member; and
aircraft cockpit area for detecting vision obscured emergencies;
switching between operating modes to supply respiratory gas to the aircraft crew member upon detection of the parameters by the at least one first set of sensors, wherein the operating modes comprise a dilution mode, an emergency mode, and a recirculation mode;
detecting, by at least one second set of sensors, a portion of the cockpit area viewed by an aircraft crew member wearing an augmented reality visor during the vision obscured emergency upon detection of the vision obscured emergency by the at least one first set of sensors;
projecting a prestored image associated with the portion of the cockpit area in front of the augmented reality visor; and
superimposing the prestored image over the portion of the cockpit area viewed by the aircraft crew member, wherein the superimposed prestored image being viewed by the aircraft crew member through the augmented reality visor to identify one or more objects in the portion of the cockpit area during the vision obscured emergency.

18. The method of claim 17, wherein the parameters that cause respiratory disorder to the aircraft crew member is selected from the group consisting of presence of smoke in the cockpit area, pressure level inside the cockpit area, and contaminants present in the cockpit ambient air, breathing rate of the aircraft crew member in an aircraft, carbon dioxide level present in exhaled gas of the aircraft crew member, partial pressure of oxygen present in blood of the aircraft crew member, and tissue oxygen saturation of the aircraft crew member.

19. The method of claim 17, wherein the respiratory gas comprises one of oxygen during the emergency mode, a combination of exhaled gas and oxygen during the recirculation mode and one of a combination of the cockpit ambient air and the cockpit ambient air mixed with oxygen during the dilution mode.

20. The method of claim 17, wherein switching between operating modes to supply respiratory gas to the aircraft crew member when the at least one first set of sensors senses the parameters that cause respiratory disorder to the aircraft crew member, comprises:
switching to the emergency mode when at least one emergency condition occurs, wherein the at least one emergency condition comprises presence of smoke in the cockpit area, pressure level inside the cockpit area is higher than as predetermined pressure level, partial pressure of oxygen present in blood of the aircraft crew member is lower than a predetermined partial pressure of the oxygen, carbon dioxide level present in exhaled gas is higher than a predetermined carbon dioxide level, breathing rate of the aircraft crew member is deviated from a predetermined breathing rate, and tissue oxygen saturation of the aircraft crew member is lower than a predetermined tissue oxygen saturation.

21. The method of claim 17, switching between operating modes to supply respiratory gas to the aircraft crew member when the at least one first set of sensors senses the parameters that cause respiratory disorder to the aircraft crew member, comprises:
    switching to the recirculation mode when a percentage of oxygen in blood of the aircraft crew member is at least 94%, carbon dioxide level present in exhaled gas is lower than a predetermined carbon dioxide level, and breathing rate of the aircraft crew member is higher than a predetermined breathing rate.

22. The method of claim 17, switching between operating modes to supply respiratory gas to the aircraft crew member when the at least one first set of sensors senses the parameters that cause respiratory disorder to the aircraft crew member, comprises:
    switching to the dilution mode when at least one condition occurs, wherein the at least one condition comprises no smoke present in the cockpit area, pressure level inside the cockpit area is higher than a predetermined pressure level, breathing rate of the aircraft crew member is equal to a predetermined breathing rate, carbon dioxide level present in exhaled gas is equal to a predetermined carbon dioxide level, and partial pressure of the oxygen present in blood of the aircraft crew member is equal to a predetermined partial pressure of oxygen.

23. The method of claim 17, wherein projecting a prestored image associated with the portion of the cockpit area in front of the augmented reality visor is based on a distance between the aircraft crew member and the portion of the cockpit area.

24. The method of claim 17, wherein the portion of the cockpit area comprises at least one control on a control panel in the cockpit area of the aircraft.

25. The method of claim 17, wherein the prestored image comprises an image of the at least one control on the cockpit area of the aircraft along with identifiers and or functional information of the at least one control.

26. The method of claim 17, wherein superimposing the prestored image over the portion of the cockpit area viewed by the aircraft crew member, comprising:
    detecting edges of the portion of the cockpit area using the at least one second set of sensors; and
    aligning the projected prestored image of the portion of the cockpit area over the portion of the cockpit area viewed by the aircraft crew member.

27. The method of claim 17, further comprising:
    overlaying a plurality of control commands or procedural instructions on the augmented reality visor to enable the aircraft crew member to select one or more control commands or a procedural instruction.

28. The method of claim 27, further comprising:
    tracking pupil of the aircraft crew member to navigate the aircraft crew member through the control commands overlaid on the augmented reality visor based on the tracking information and the one or more control commands or the procedural instruction selected by the aircraft crew member.

29. The method of claim 27, further comprising:
    reading out the plurality of overlaid control commands or the procedural instructions using an audio output device.

\* \* \* \* \*